(12) United States Patent
Kim

(10) Patent No.: US 10,052,181 B2
(45) Date of Patent: Aug. 21, 2018

(54) COSMETIC DENTAL PROCESS

(76) Inventor: Jason J. Kim, Manhasset, NY (US)

( * ) Notice: Subject to any disclaimer, the term of this patent is extended or adjusted under 35 U.S.C. 154(b) by 48 days.

(21) Appl. No.: 13/285,315

(22) Filed: Oct. 31, 2011

(65) Prior Publication Data

US 2013/0108989 A1 May 2, 2013

(51) Int. Cl.
*A61C 13/107* (2006.01)
*A61C 5/20* (2017.01)

(52) U.S. Cl.
CPC ............ *A61C 13/0001* (2013.01); *A61C 5/20* (2017.02)

(58) Field of Classification Search
CPC ........ A61C 13/0001; A61C 5/002; A61C 5/20
USPC ...................... 433/202.1, 191–196, 218–219, 433/222.1–223, 226, 204, 212.1, 213–215
See application file for complete search history.

(56) References Cited

U.S. PATENT DOCUMENTS

| | | | | |
|---|---|---|---|---|
| 3,987,545 A | * | 10/1976 | Kennedy | 433/36 |
| 4,226,593 A | * | 10/1980 | Cohen et al. | 433/226 |
| 4,822,278 A | * | 4/1989 | Oliva | A61C 3/00 |
| | | | | 294/189 |
| 6,964,985 B2 | * | 11/2005 | Karim et al. | 523/115 |
| 7,217,131 B2 | * | 5/2007 | Vuillemot | 433/215 |
| 7,442,040 B2 | * | 10/2008 | Kuo | 433/202.1 |
| 2005/0227204 A1 | * | 10/2005 | Hauck | A61C 5/20 |
| | | | | 433/218 |
| 2008/0299510 A1 | * | 12/2008 | Penchas et al. | 433/34 |
| 2012/0028210 A1 | * | 2/2012 | Hegyi et al. | 433/34 |

FOREIGN PATENT DOCUMENTS

WO WO 2011/156806 A1 * 12/2011

* cited by examiner

*Primary Examiner* — Edward Moran
(74) *Attorney, Agent, or Firm* — Greenberg Traurig, LLP

(57) ABSTRACT

The present invention provides a process for use in improving the appearance of a patient's teeth having plurality of defects. More particularly, the process involves obtaining a cast having a plurality of teeth portions corresponding to the patient's teeth. The cast include a plurality of defects corresponding to the defects of the patient's teeth. A first material is applied to the tooth portions of the cast to correct the defects in the cast and to form a modified version of the cast without removing any of the cast material from any of the tooth portions of the cast. A mold is made using the modified version of the cast. The mold is used in applying a second material to the patient's teeth for creating a temporary modified look directly on the patient's teeth for viewing by the patient.

22 Claims, 4 Drawing Sheets

COSMETIC DENTAL PROCESS

FIELD OF THE INVENTION

The present invention relates to a cosmetic dental process, and, more particularly, to a cosmetic dental process useful in providing a temporary modified look directly on a patient's teeth.

BACKGROUND OF THE INVENTION

Cosmetic dental procedures have gained popularity to improve the appearance of patients' teeth. Some procedures involve shaping one or more of a patient's original teeth and covering the teeth with appropriately shaped/sized porcelain veneers, crowns or the like so as to achieve a desired appearance. Prior to proceeding with a cosmetic dental procedure, a patient may be provided with one or more computer-generated images showing how his/her teeth would appear after its completion. However, the patient may not be able to accurately discern from the computer-generated images the actual look of his/her teeth after the performance of the procedure.

SUMMARY OF THE INVENTION

The present invention provides a process for use in improving the appearance of a patient's teeth having a plurality of defects, such as voids, including a gap formed between an adjacent pair of the teeth, a cut formed in a chipped one of the teeth, a space formed around a misaligned one of the teeth due to its misalignment relative to an adjacent one of the teeth, and a space formed around a misshaped one of the teeth. More particularly, the process involves obtaining a cast formed from a cast material and having a plurality of teeth portions corresponding to the patient's teeth. Because the cast is basically an exact copy of the patient's teeth, the cast includes a plurality of defects corresponding to the defects of the patient's teeth. A first material is applied to at least one of the tooth portions of the cast to correct at least one of the defects in the cast and to thereby form a modified version of the cast without decreasing original sizes and shapes of the tooth portions of the cast (e.g., without substantially removing the cast material from the tooth portions of the cast). At least one mold is made using the modified version of the cast. The at least one mold is used in applying a second material to the patient's teeth for creating a temporary modified look directly on the patient's teeth. Thereafter, if the patient decides to proceed with an actual cosmetic dental procedure, his/her teeth are prepared, and appropriately sized and/or shaped veneers or other coverings are affixed thereto.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

Figure 1:
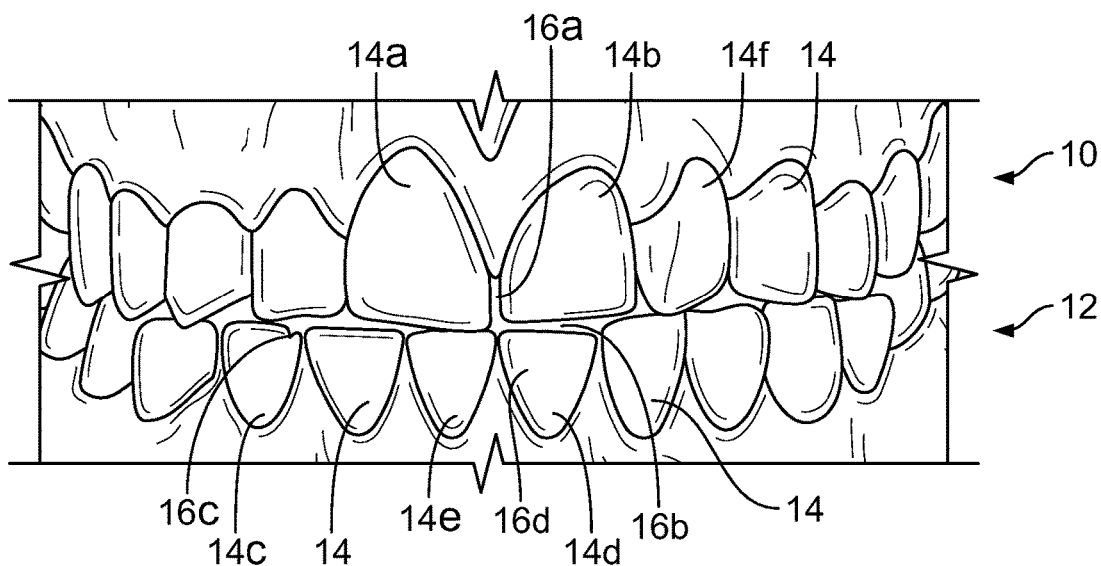
FIG. 1 is a view of portions of upper and lower rows of a patient's teeth.
Figure 2:
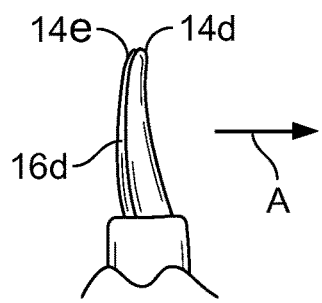
FIG. 2 is a side view of an adjacent pair of the teeth shown in FIG. 1.

With reference to FIG. 1, shown therein are portions of upper and lower rows 10, 12 of a patient's teeth 14. The teeth 14 include one or more defects or imperfections, which can be cosmetic, as well as structural. More particularly, the defects can include a plurality of voids, such a gap 16a formed between an adjacent pair 14a, 14b of the teeth 14, a space 16b formed around (e.g., below) the tooth 14b, which is misaligned vertically relative to its tooth 14a, a cut 16c formed in a chipped one 14c of the teeth 14, a space 16d (see also FIG. 2) formed by a misaligned one 14d of the teeth 14, which is misaligned relative to an adjacent one 14e of the teeth 14 transversely (i.e., in a direction generally perpendicular to the front surface of the misaligned tooth 14d as indicated by arrow A in FIG. 2), a misshaped one 14f of the teeth 14, etc. The defects can include other types of cosmetic and/or structural defects or imperfections. The present invention provides a process for repairing the defects and thereby enhancing the appearance of the patient's teeth. More particularly, the process involves applying a temporary filler material directly to the teeth 14 over the defects with the use of a pre-formed mold such that the patient can see how his/her teeth 14 would appear after the performance of an actual repair procedure. The process will be described in detail below.

Still referring to FIG. 1, impressions or imprints (not shown) of the upper and lower rows 10, 12 of the patient's teeth 14 are taken by a dentist or another professional. For instance, the impressions can be taken using a conventional impression tray (not shown) containing a conventional impression material, such as an arginate material. Using the impressions, a cast or study model 18 (see FIG. 3) corresponding to the teeth 14 is formed as is done conventionally in the art. The cast 18 can be made at the dentist's office using a conventional cast material. Alternatively, the impressions can be sent to a remote dental laboratory or the like for the fabrication of the cast 18.

Figure 3:
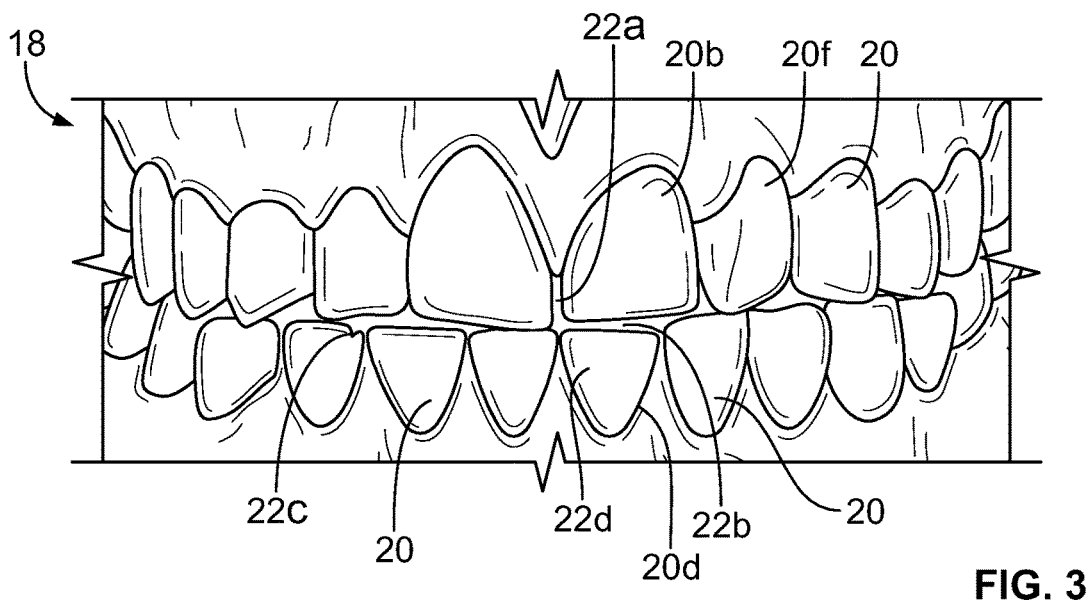
FIG. 3 is a view of portions of upper and lower sections of a cast corresponding to the teeth shown in FIG. 1.

Referring to FIG. 3, in which only portions of upper and lower sections of the cast 18 are shown, the cast 18 is basically an identical copy of the patient's teeth 14 and includes teeth portions 20, each of which is substantially identical, in size and shape, to a corresponding one of the patient's original teeth 14. As a result, the cast 18 includes defects substantially identical to those included in the original teeth 14. For instance, the cast 18 contains a gap 22a, which corresponds to the gap 16a of the teeth 14, a space 22b, which corresponds to the space 16b of the teeth 14, a cut 22c, which corresponds to the cut 16c of the teeth 14, a space 22d, which corresponds to the space 16d of the teeth 14, and a tooth portion 20f, which corresponds to the misshaped tooth 14f. Once the cast 18 is made, it is sent to a dental laboratory or the like for further processing, as will be discussed below.

Figure 4:
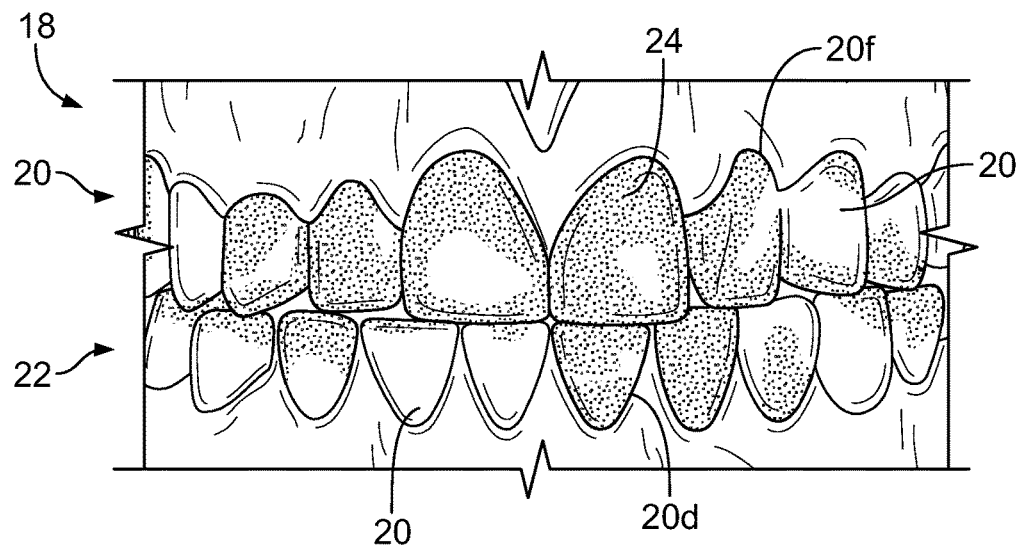
FIG. 4 is a view similar to FIG. 3, except that dental wax has been applied to the cast to modify its tooth appearance.
Figure 4A:
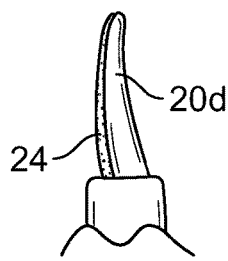
FIG. 4a is a side view of an adjacent pair of tooth portions of the cast shown in FIG. 4.

The cast 18 is studied or otherwise evaluated by a dental professional (e.g., a dental technician) for the purpose of improving the appearance of the patient's teeth 14. More particularly, dental wax 24 (as indicated by the shaded areas in FIG. 4) is selectively applied to the teeth portions of the cast 18 to and/or over the imperfections without removing any original cast material from any of the tooth portions 20 of the cast 18. In other words, the original sizes and shapes of the tooth portions 20 are not reduced or decreased during the performance of this process. Instead, the dental wax 24 is applied to the cast 18 to only build upon the original tooth form of the cast 18. For instance, the dental wax 24 is applied to fill, and thereby close off, the gap 22a and the cut 22c. The dental wax 24 is also applied to the tooth portion 20b that corresponds to the tooth 14b of the patient so as to fill the space 22b, as well as to a front surface of the tooth portion 20d that corresponds to the tooth 14d of the patient so as to fill the space 22d (see also FIG. 4a). Moreover, the dental wax 24 is selectively applied to the tooth portion 20f corresponding to the tooth 14f for reshaping same appropriately.

It should be noted that the cast material may be removed from the tooth portions 20 of the cast 18 so long as their original sizes and shapes are not reduced or decreased. For instance, if the cast material is accidentally removed from an area of the tooth portions 20, that area can be repaired with the dental wax 24 to bring it back to its original shape and size. It should also be noted that the dental wax 24 can be replaced with any conventional materials that can be used to modify the structure of the cast 18.

Figure 5:
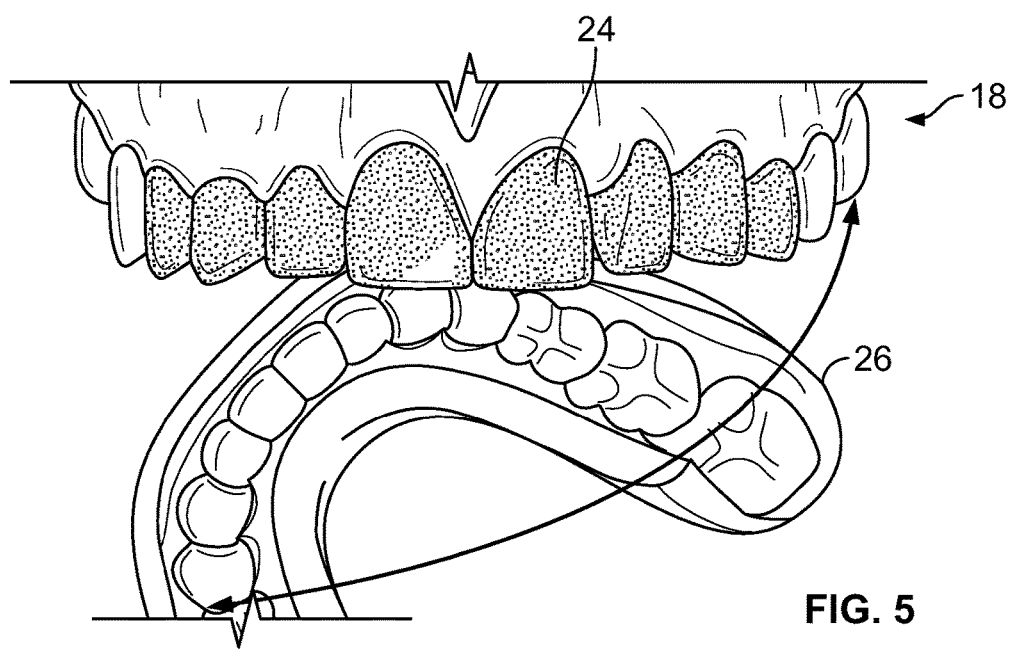
FIG. 5 is a view illustrating the formation of a mold corresponding to the upper section of the cast shown in FIG. 4.

Once the cast 18 has been modified as discussed above, upper and lower molds 26 (only one of which is shown in FIG. 5) corresponding to the upper and lower sections, respectively, of the teeth portions 20 of the cast 18 are formed in a conventional manner. More particularly, conventional putty impression materials (not shown) are applied to the upper and lower rows of the cast 18 manually or via a dental tray. After the impression materials harden, they are removed from the cast 18 and form the molds 26.

Figure 6:
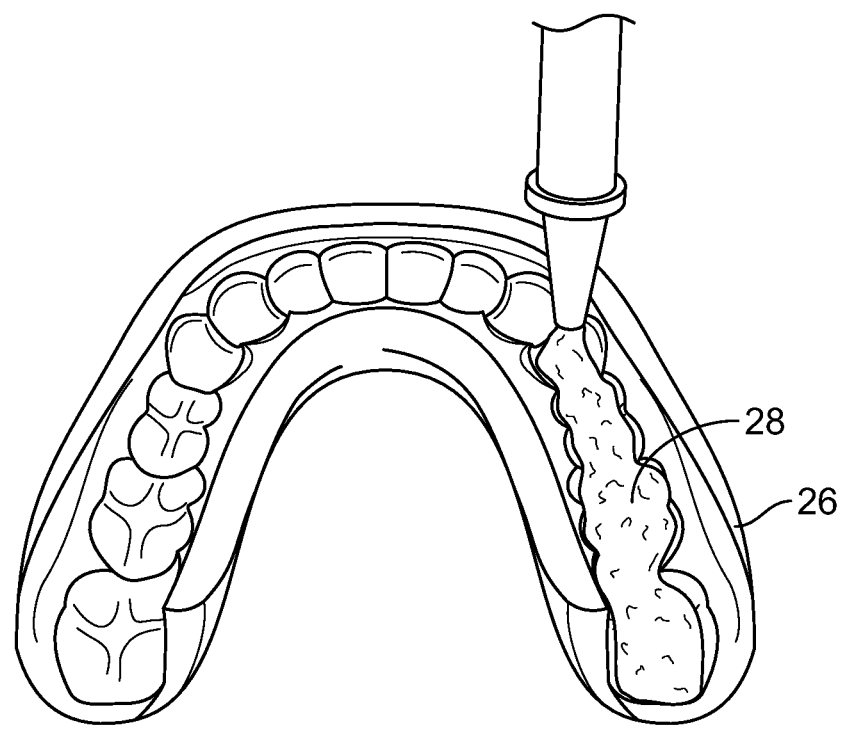
FIG. 6 is a view of the mold shown in FIG. 5, the mold being filled with a filler material for application to the teeth of the patient.

Once the molds 26 have been fabricated, they are sent to the dentist for use in creating a temporary modified look directly on the patient's teeth. More particularly, a self-curing filler material 28 is placed in each of the molds 26 (see FIG. 6). The filler material 28 can be any self-curing material that is capable of at least temporarily adhering to tooth surfaces (e.g., any conventional materials used to create temporaries, such as the material sold under the trademark "LUXATEMP" by DMG America located in Englewood, N.J.). The filler material 28 can also be soft and allow it to be peeled off easily from applied tooth surfaces after curing. The filler material 28 can be selected by the dentist such that its color closely matches that of the patient's teeth 14.

Figure 7:
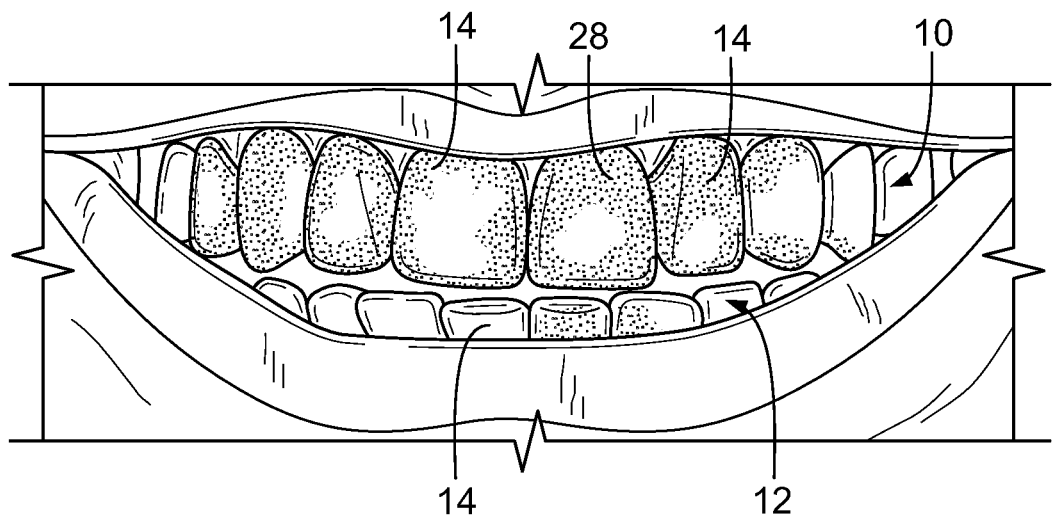
FIG. 7 is a view of the patient's teeth after the application of the filler material with the use of the mold shown in FIG. 5.
Figure 8A:
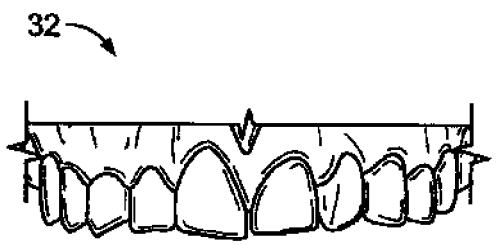
FIGS. 8a and 8b are views comparing the appearance of the original teeth to the appearance of the teeth applied with the filler material.
Figure 8B:
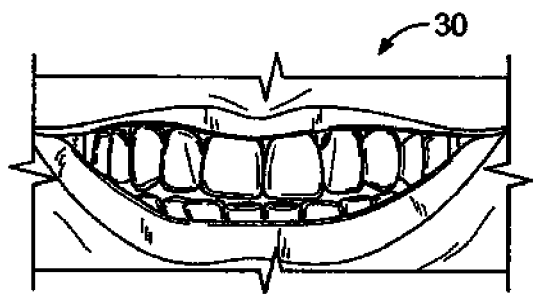

The molds 26 filled with the filler material 28 are applied to the upper and lower rows 10, 12 of the patient's original teeth 14. Because the molds 26 are formed from the cast 18, which is made by only applying the dental wax 24 thereto (i.e., none of the original tooth form has been removed from the cast 18), the molds 26 include spaces corresponding to the shapes of the patient's original teeth, as well as spaces created by the addition of the dental wax 24 to the cast 18. As a result, the molds 26 can be fitted over the upper and lower rows 10, 12 of the patient's teeth 14. The molds 26 remain applied to the teeth 14 for a predetermined time period to allow the filler material 28 to cure and adhere to the patient's teeth 14. After the lapse of the time period, the molds 26 are removed from the teeth 14 of the patient, leaving the filler material 28 on the teeth 14 and covering up their defects (see FIG. 7). For instance, the filler material 28 fills the gap 16a, the cut 16c and the spaces 16b, 16d. Moreover, the filler material 28 is applied to the misshaped tooth 14f to change its overall shape. After the molds 26 have been removed, the dentist prepares a temporary look of the patient's teeth 14 by selectively removing excess filler material 28 from the teeth 14. Once the temporary look has been prepared (see FIG. 7), the patient can view same directly from his/her teeth 14. A photograph 30 of the temporary look (see FIG. 8b) may be taken and compared to a previously taken photograph 32 of the patient's original tooth 14 (see FIG. 8a). Thereafter, the filler material 28 is removed from the patient's teeth 14 by the dentist r by the patient.

Figure 9:
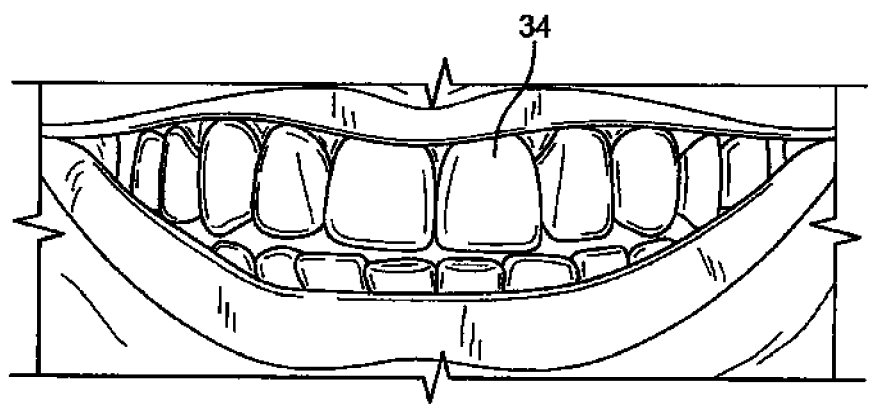
FIG. 9 is a view of the patient's teeth after the performance of a cosmetic dental procedure, wherein veneers are applied to the teeth.

Based on the temporary look, the patient may decide to proceed with an actual cosmetic dental procedure. If such a decision is made, the patient's teeth 14 are prepared (e.g., shaved or filed) in a conventional manner, and impressions of the prepared teeth 14 are taken and sent to a dental laboratory. Thereafter, appropriate veneers or other coverings, such as crowns and the like, 34 (see FIG. 9) are formed by a dental technician in a conventional manner using the impressions and a cast formed with the use thereof. After the veneers 34 have been formed, they are sent to the dentist and affixed to the patient's prepared teeth 14 in a conventional manner.

The present invention provides numerous advantages over the prior art. For instance, a temporary modified look can be viewed directly from a patient's teeth without permanently modifying the teeth. That is, because the molds 26 are prepared from the cast 18 which retains the patient's original tooth form (e.g., none of the cast material is removed from the cast 18 during its modification via the application of the wax material 24), the molds 26 can be fitted directly over or to the patient's teeth without the teeth undergoing any preparatory work, thereby providing a convenient way to view a modified look of a person's teeth before undergoing an actual cosmetic dental procedure.

The present invention can have numerous modifications and variations. For instance, the impressions of the patient's original teeth 14 can be taken by the patient himself and then sent to a dental laboratory. The molds 26 can also be provided directly to the patient together with the filler material 28 as a kit so that the patient can apply the filler material 28 to his teeth 14 without the assistance of any dental professional.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined in the appended claims.

What is claimed is:
1. A process for use in improving the appearance of a patient's teeth, some of which have a plurality of defects, said process comprising the steps of:
    taking, at a customer location, at least one impression of the patient's teeth;

receiving, from a dental laboratory located remotely from the customer location, at least one mold, the at least one mold being made at the dental laboratory by a process comprising the steps of:
  forming a cast of the patient's teeth from a cast material using the at least one impression, the cast having a plurality of teeth portions corresponding to the patient's teeth and a plurality of defects corresponding to the defects of the patient's teeth;
  applying a first material to at least one of the tooth portions of the cast to correct at least one of the defects in the cast and to thereby form a modified version of the cast without decreasing original sizes and shapes of the tooth portions of the cast; and
  making the at least one mold using the modified version of the cast, said making step consisting of the steps of applying a putty material to the modified version of the cast, allowing the putty material to harden and removing the at least one mold from the modified version of the cast, the at least one mold consisting of the hardened putty material after its removal from the modified version of the cast; and
applying, at the customer location, a second hardenable material to the patient's teeth using the at least one mold without permanently modifying the patient's teeth for creating a temporary modified look directly on the patient's teeth, wherein only the second hardenable material is applied to the patient's teeth via the at least one mold during the performance of said step of applying the second hardenable material to the patient's teeth.

2. The process of claim 1, wherein said step of applying the second hardenable material to the patient's teeth includes the steps of placing the second hardenable material in the at least one mold; placing the at least one mold containing the second hardenable material over the patient's teeth such that the second hardenable material is applied to the patient's teeth so as to cover up the defects therein; and removing the at least one mold from the patient's teeth after the curing of the second hardenable material, the second hardenable material being the only material remaining on the patient's teeth after the removal of the at least one mold from the patient's teeth.

3. The process of claim 2, wherein the second hardenable material includes a peelable material such that the second hardenable material can be peeled off the patient's teeth after inspection.

4. The process of claim 1, wherein said applying step is performed without removing the cast material from the tooth portions of the cast.

5. The process of claim 1, wherein the defects of the cast include a plurality of voids; and wherein said applying step includes the step of filling the voids with the first material without removing any cast material from any of the tooth portions of the cast.

6. The process of claim 5, wherein the voids include at least one of a gap formed between an adjacent pair of the tooth portions, a cut formed in a first one of the tooth portions, a space formed around a second one of the tooth portions due to its misalignment relative to an adjacent one of the tooth portions, and a space formed around a misshaped one of the tooth portions.

7. The process of claim 1, further comprising the step of making a plurality of coverings that can be permanently applied to the patient's teeth so as to correct the defects in the patient's teeth.

8. The process of claim 7, further comprising the step of applying the coverings to the patient's teeth, the coverings including a plurality of veneers.

9. The process of claim 1, wherein the first material includes a wax material.

10. The process of claim 1, wherein the second hardenable material is applied to the patient's teeth without preparing the patient's teeth.

11. The process of claim 1, further comprising the step of sending the at least one impression of the patient's teeth from the customer location to the dental laboratory after the performance of said taking step, wherein the customer location is a dentist's office or a patient's place.

12. A process for use in improving the appearance of a patient's teeth, some of which have a plurality of defects, said process comprising the steps of:
  taking, at a customer location, at least one impression of the patient's teeth;
  forming, at a dental laboratory located remotely from the customer location, a cast of the patient's teeth from a cast material using the at least one impression, the cast having a plurality of teeth portions corresponding to the patient's teeth and a plurality of defects corresponding to the defects of the patient's teeth;
  applying, at the dental laboratory, a first material to at least one of the tooth portions of the cast to correct at least one of the defects in the cast and to thereby form a modified version of the cast without decreasing original sizes and shapes of the tooth portions of the cast;
  making, at the dental laboratory, at least one mold using the modified version of the cast, said making step consisting of the steps of applying a putty material to the modified version of the cast, allowing the putty material to harden and removing the at least one mold from the modified version of the cast, the at least one mold consisting of the hardened putty material after its removal from the modified version of the cast; and
  applying, at the customer location, a second hardenable material to the patient's teeth using the at least one mold without permanently modifying the patient's teeth for creating a temporary modified look directly on the patient's teeth, wherein only the second hardenable material is applied to the patient's teeth via the at least one mold during the performance of said step of applying the second hardenable material to the patient's teeth.

13. The process of claim 12, wherein said step of applying the second hardenable material to the patient's teeth includes the steps of placing the second hardenable material in the at least one mold; placing the at least one mold containing the second hardenable material over the teeth such that the second hardenable material is applied to the patient's teeth so as to cover up the defects therein; and removing the at least one mold from the patient's teeth after the curing of the second hardenable material, the second hardenable material being the only material remaining on the patient's teeth after the removal of the at least one mold from the patient's teeth, the second hardenable material including a peelable material such that the second hardenable material can be peeled off the patient's teeth after inspection.

14. The process of claim 12, wherein said step of applying the first material to the at least one of the tooth portions of the cast is performed without removing the cast material from the tooth portions of the cast.

15. The process of claim 12, wherein the defects of the cast include a plurality of voids; and wherein said step of applying the first material to the at least one of the tooth portions of the cast includes the step of filling the voids with the first material without removing any cast material from any of the tooth portions of the cast.

16. The process of claim 15, wherein the voids include at least one of a gap formed between an adjacent pair of the tooth portions, a cut formed in a first one of the tooth portions, a space formed around a second one of the tooth portions due to its misalignment relative to an adjacent one of the tooth portions, and a space formed around a misshaped one of the tooth portions.

17. The process of claim 12, further comprising the steps of making a plurality of coverings that can be permanently applied to the patient's teeth so as to correct the defects in the patient's teeth.

18. The process of claim 17, further comprising the step of applying the coverings to the patient's teeth.

19. The process of claim 18, wherein the coverings include a plurality of porcelain veneers.

20. The process of claim 12, wherein the second hardenable material is applied to the patient's teeth without preparing the patient's teeth.

21. The process of claim 12, further comprising the step of placing the second hardenable material in the at least one mold prior to the performance of said step of applying the second hardenable material to the patient's teeth, said step of applying the second hardenable material to the patient's teeth including the step of placing the at least one mold containing the second hardenable material on the patient's teeth so as to apply the second hardenable material to the patient's teeth.

22. The process of claim 12, further comprising the step of sending the at least one impression of the patient's teeth from the customer location to the dental laboratory after the performance of said taking step, wherein the customer location is a dentist's office or a patient's place.

\* \* \* \* \*